United States Patent
Arinobe et al.

(10) Patent No.: US 12,296,143 B2
(45) Date of Patent: May 13, 2025

(54) LIQUID MEDICINE ADMINISTRATION DEVICE

(71) Applicant: TERUMO KABUSHIKI KAISHA, Tokyo (JP)

(72) Inventors: Manabu Arinobe, Kanagawa (JP); Yusuke Hyakkan, Kanagawa (JP); Minami Maekawa, Kanagawa (JP); Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 819 days.

(21) Appl. No.: 17/487,093

(22) Filed: Sep. 28, 2021

(65) Prior Publication Data

US 2022/0008650 A1 Jan. 13, 2022

Related U.S. Application Data

(63) Continuation of application No. PCT/JP2020/006288, filed on Feb. 18, 2020.

(30) Foreign Application Priority Data

Mar. 29, 2019 (JP) .................................. 2019-066307

(51) Int. Cl.
*A61M 5/145* (2006.01)
*A61M 5/142* (2006.01)
(Continued)

(52) U.S. Cl.
CPC ...... *A61M 5/1452* (2013.01); *A61M 5/14236* (2013.01); *A61M 5/172* (2013.01);
(Continued)

(58) Field of Classification Search
CPC .... A61M 5/50; A61M 5/5066; A61M 5/5073; A61M 2005/14533; A61M 2205/103;
(Continued)

(56) References Cited

U.S. PATENT DOCUMENTS 5,176,646 A 1/1993 Kuroda
5,236,416 A 8/1993 McDaniel et al.
(Continued)

FOREIGN PATENT DOCUMENTS

JP 2015181835 A 10/2015
TW 520995 B * 4/2001
WO 2017051619 A1 3/2017

OTHER PUBLICATIONS

International Search Report (PCT/ISA/210) with translation and Written Opinion (PCT/ISA/237) mailed on Apr. 7, 2020, by the Japanese Patent Office as the International Searching Authority for International Application No. PCT/JP2020/006288. (8 pages).

*Primary Examiner* — Phillip A Gray
*Assistant Examiner* — Forrest Blake Dipert
(74) *Attorney, Agent, or Firm* — BUCHANAN INGERSOLL & ROONEY PC

(57) ABSTRACT

This liquid medicine administration device includes a liquid medicine container, a gasket for expelling the liquid medicine in the liquid medicine container, a plunger that moves the gasket, a housing, a drive mechanism that advances the plunger, and a rotation restriction unit that restricts rotation of the plunger. The drive mechanism includes a motor and a feed screw. The plunger includes: a threaded portion threadedly engaged with the feed screw; and a plunger body that advances with feed screw rotation and that moves the gasket, while rotation of the plunger relative to the housing is restricted by the rotation restriction unit. The plunger includes a canceling mechanism that cancels transmission of a pressing force from the plunger body to the gasket when the plunger body receives an axial reaction force equal to or greater than a preset pressing force from the gasket during advancement with the feed screw rotation.

20 Claims, 10 Drawing Sheets

(51) Int. Cl.
  *A61M 5/168*  (2006.01)
  *A61M 5/172*  (2006.01)
(52) U.S. Cl.
  CPC ............... *A61M 5/14248* (2013.01); *A61M 2005/16863* (2013.01); *A61M 2205/3327* (2013.01); *A61M 2205/3365* (2013.01)
(58) Field of Classification Search
  CPC ............ A61M 5/14236; A61M 5/145; A61M 5/1452; A61M 5/1456; A61M 5/14566; A61M 5/16831; A61M 5/16854; A61M 5/31501; A61M 5/31528; A61M 5/3156; A61M 5/31561; A61M 5/31563
  See application file for complete search history.

(56) References Cited

U.S. PATENT DOCUMENTS

| | | | |
|---|---|---|---|
| 2004/0085215 A1* | 5/2004 | Moberg | A61M 39/12 604/131 |
| 2004/0176725 A1* | 9/2004 | Stutz, Jr. | A61M 5/1456 604/155 |
| 2011/0009821 A1* | 1/2011 | Jespersen | A61M 5/1452 604/131 |
| 2018/0207358 A1 | 7/2018 | Uchiyama et al. | |

\* cited by examiner

# LIQUID MEDICINE ADMINISTRATION DEVICE

CROSS-REFERENCES TO RELATED APPLICATIONS

This application is a continuation of International Patent Application No. PCT/JP2020/006288 filed on Feb. 18, 2020, which claims priority to Japanese Patent Application No. 2019-066307 filed on Mar. 29, 2019, the entire content of both of which is incorporated herein by reference.

FIELD OF THE INVENTION

The present invention generally relates to a liquid medicine administration device.

BACKGROUND DISCUSSION

Conventionally, a syringe pump type liquid medicine administration device has been known which administers a liquid medicine, with which a liquid medicine container is filled, into a living body by a pressing action of a plunger. The plunger can be configured to, for example, discharge the liquid medicine from the liquid medicine container when pushed into the liquid medicine container by a rotational driving force of a drive mechanism.

For example, Japanese Patent Application Publication No. 2015-181835 discloses a drive mechanism including a motor that generates a rotational driving force, a gear reduction mechanism that decreases the speed of rotation of the motor, and a feed screw that rotates in response to torque from the gear reduction mechanism. The plunger is configured as a bearing of the feed screw, and is also configured to advance by rotation of the feed screw.

SUMMARY

However, in the liquid medicine administration device as described above, when blockage occurs in a liquid delivery path of the liquid medicine, a load is applied to a region on the upstream side of the blockage portion in the liquid delivery path by the plunger that is going to advance. As a result, the liquid medicine may leak out in the region upstream of the blockage portion in the liquid delivery path.

The liquid medicine administration device disclosed here is capable of preventing leakage of a liquid medicine when blockage occurs in a liquid delivery path of the liquid medicine.

A liquid medicine administration device includes: a liquid medicine container filled with a liquid medicine and having, at a tip, an opening through which the liquid medicine is discharged; a gasket for expelling the liquid medicine in the liquid medicine container, the gasket being slidable on an inner wall of the liquid medicine container; a plunger connected to the gasket; a housing that holds the liquid medicine container and the plunger; a drive mechanism that advances the plunger toward the tip of the liquid medicine container; and a rotation restriction unit that restricts rotation of the plunger with respect to the housing. The drive mechanism includes a motor and a feed screw that rotates in response to rotation of the motor, and the plunger includes: a threaded portion threadedly engaged with the feed screw; and a plunger body that advances with the rotation of the feed screw and that presses the gasket, while the rotation of the plunger with respect to the housing is being restricted by the rotation restriction unit. The plunger is provided with a canceling mechanism that cancels transmission of a pressing force from the plunger body to the gasket when the plunger body receives an axial reaction force equal to or greater than a preset pressing force from the gasket during advancement with the rotation of the feed screw.

The liquid medicine administration device is able to prevent leakage of the liquid medicine when blockage occurs in a liquid delivery path of the liquid medicine.

Another aspect of the disclosure involves a method comprising inserting a needle tube into a living body, wherein the needle tube is connected to a liquid medicine container containing liquid medicine so that sliding movement of a gasket connected to a plunger and positioned in the liquid medicine container causes the liquid medicine to flow from the liquid medicine container to the needle tube. The liquid medicine container is housed in a housing together with a motor that outputs a drive torque and that is operatively connected to a feed screw so that the drive torque rotates the feed screw, with rotation of the plunger being restricted. The plunger includes a threaded portion and a plunger body, with the threaded portion of the plunger threadedly engaging the feed screw, and the plunger body being movable in the liquid medicine container toward the tip by virtue of the rotation of the feed screw and the restriction on rotation of the plunger. The method additionally involves operating the motor to produce the drive torque, transferring the drive torque to the feed screw to move the plunger so that the plunger body applies a pressing force to the gasket to discharge liquid medicine from the liquid medicine container by way of the tip, and cancelling the pressing force applied by the plunger body to the gasket when the plunger body receives an axial reaction force equal to or greater than a preset pressing force from the gasket so that the gasket stops moving toward the tip and the discharge of the liquid medicine from the liquid medicine container by way of the tip stops.

According to another aspect, a liquid medicine administration device comprises: a liquid medicine container filled with liquid medicine, with the liquid medicine container including a tip at which is located an opening through which the liquid medicine is discharged during administration of the liquid medicine; a gasket positioned inside the liquid medicine container and connected to a plunger, with the gasket being movable in the liquid medicine container toward the opening of the liquid medicine container to discharge the liquid medicine through the opening; a housing in which is housed the liquid medicine container and the plunger; a motor which operates to output a drive torque, with the motor being operatively connected to a feed screw so that the drive torque rotates the feed screw; and at least one guide wall that engages the plunger to restrict rotation of the plunger relative to the housing. The plunger includes a threaded portion and a plunger body, with the threaded portion of the plunger threadedly engaging the feed screw, and the plunger body being movable in the liquid medicine container toward the tip by virtue of the rotation of the feed screw that is threadedly engaged with the threaded portion of the plunger and the at least one guide wall that engages the plunger to restrict rotation of the plunger with respect to the housing. The plunger is configured so that when the plunger body receives an axial reaction force equal to or greater than a preset pressing force from the gasket during advancement of the plunger through the rotation of the feed screw, a pressing force applied by the plunger body to the gasket to advance the gasket toward the tip ceases.

DETAILED DESCRIPTION

Figure 1:
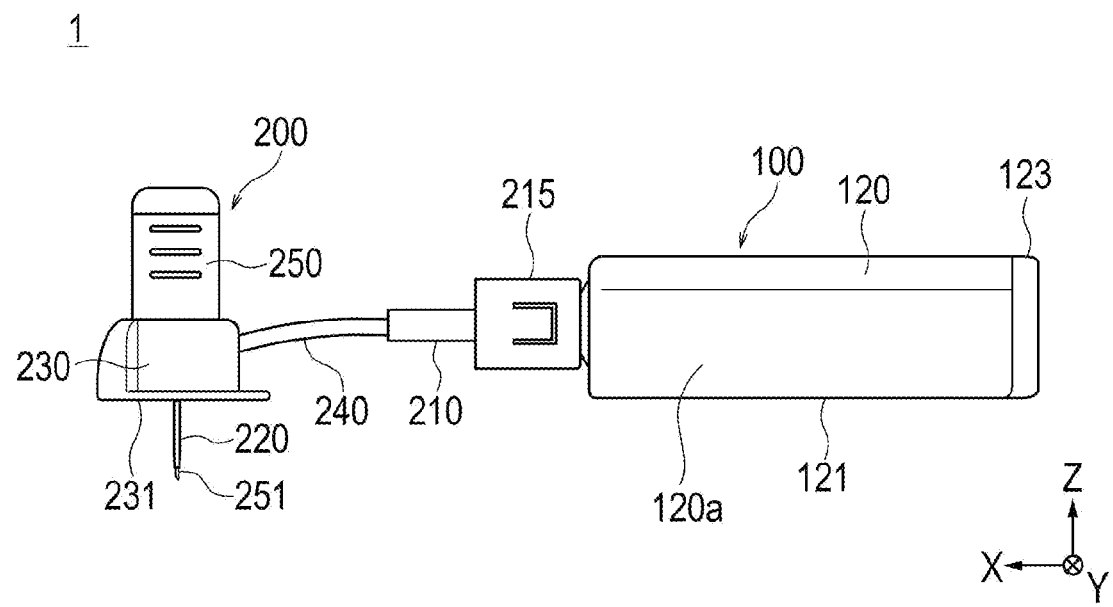
FIG. 1 is a side view of a liquid medicine administration system according to one embodiment.

Set forth below with reference to the accompanying drawings is a detailed description of embodiments of a liquid medicine administration system, a liquid medicine administration device, and an administration instrument representing examples of the inventive liquid medicine administration system, liquid medicine administration device, and administration instrument disclosed here. The dimensions or scales on the drawings may be exaggerated or different from actuality/reality for convenience of description and illustration. The following description is not intended to limit the technical scope and meanings of terms set forth in the claims. Further, the dimensional ratios in the drawings are exaggerated for convenience of description, and may differ from the actual ratios.

FIGS. 1 to 4 illustrate a liquid medicine administration system 1, a liquid medicine administration device 100, and an administration instrument 200 according to the present embodiment. FIGS. 5 to 6B are illustrations of a canceling mechanism 10 according to the present embodiment. An arrow X in each drawing indicates the "longitudinal direction (longitudinal direction of a liquid medicine container 110)" of the liquid medicine administration device 100, an arrow Y indicates the "width direction (depth direction)" of the liquid medicine administration device 100, and an arrow Z indicates the "height direction" of the liquid medicine administration device 100.

(Liquid Medicine Administration System)

The liquid medicine administration system 1 is used to administer a liquid medicine into a living body. As illustrated in FIG. 1, the liquid medicine administration system 1 includes the liquid medicine administration device 100 and the administration instrument 200.

Figure 2:
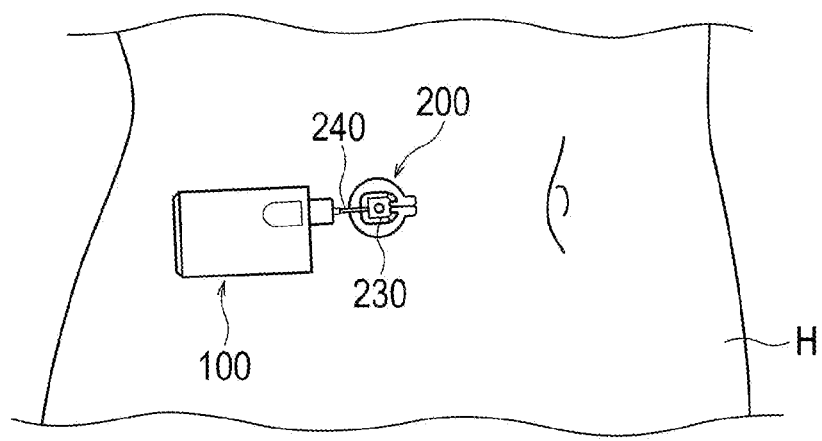
FIG. 2 is a diagram schematically illustrating an example of use of the liquid medicine administration system illustrated in FIG. 1.

As illustrated in FIG. 2, the liquid medicine administration device 100 and the administration instrument 200 are of a patch type that is attached to the body surface (skin) H of a user when used. The body part of the user to which the liquid medicine administration device 100 and the administration instrument 200 are attached is not particularly limited, and examples thereof include the abdomen and the thigh.

The liquid medicine administration system 1 can continuously administer a liquid medicine, contained in the liquid medicine container 110 included in the liquid medicine administration device 100, into a living body for relatively a long period of time (for example, several minutes to several hours) by a pressing action of a later-described plunger 130. The liquid medicine administration system 1 may administer the liquid medicine at intervals into the living body.

(Liquid Medicine Administration Device)

Figure 3:
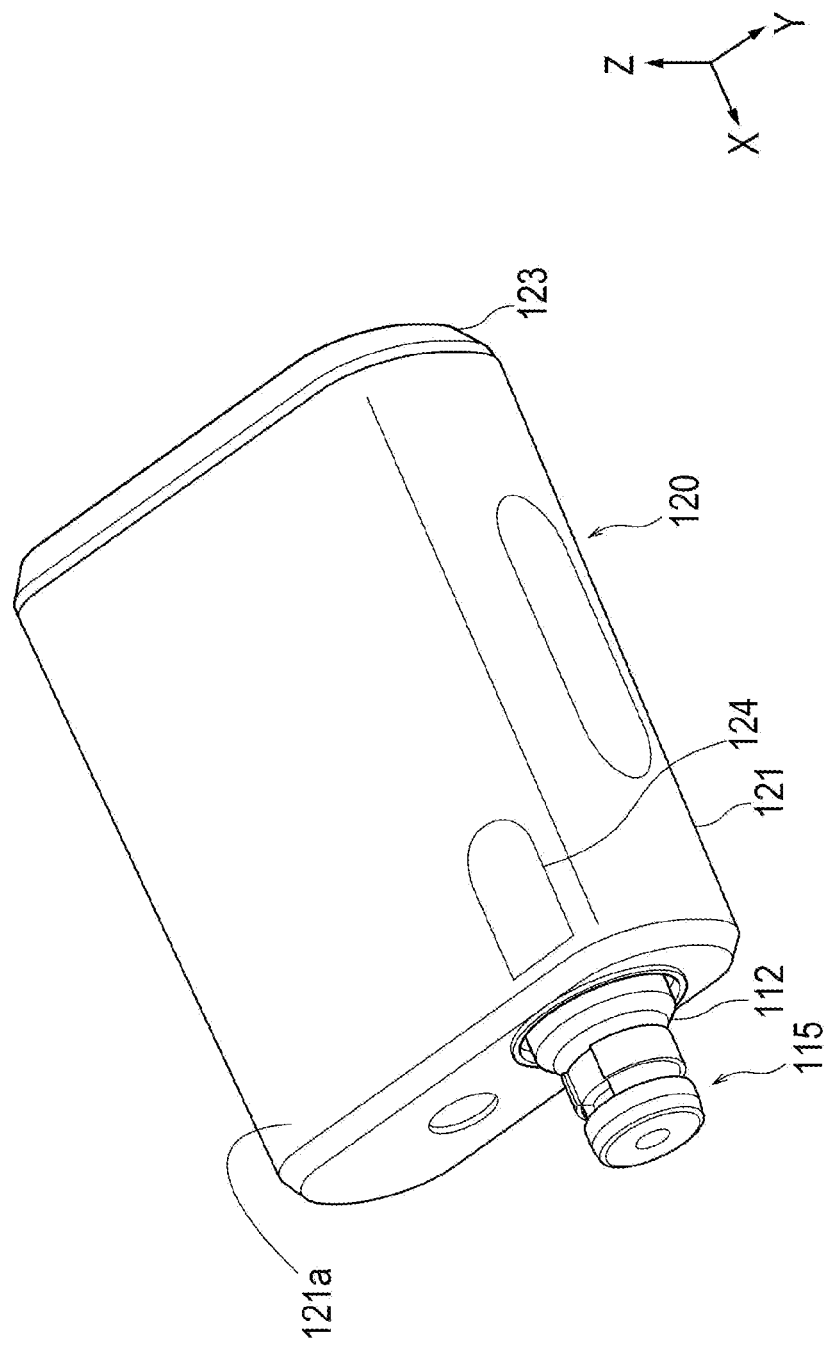
FIG. 3 is a schematic perspective view of a liquid medicine administration device constituting the liquid medicine administration system illustrated in FIG. 1.
Figure 4:
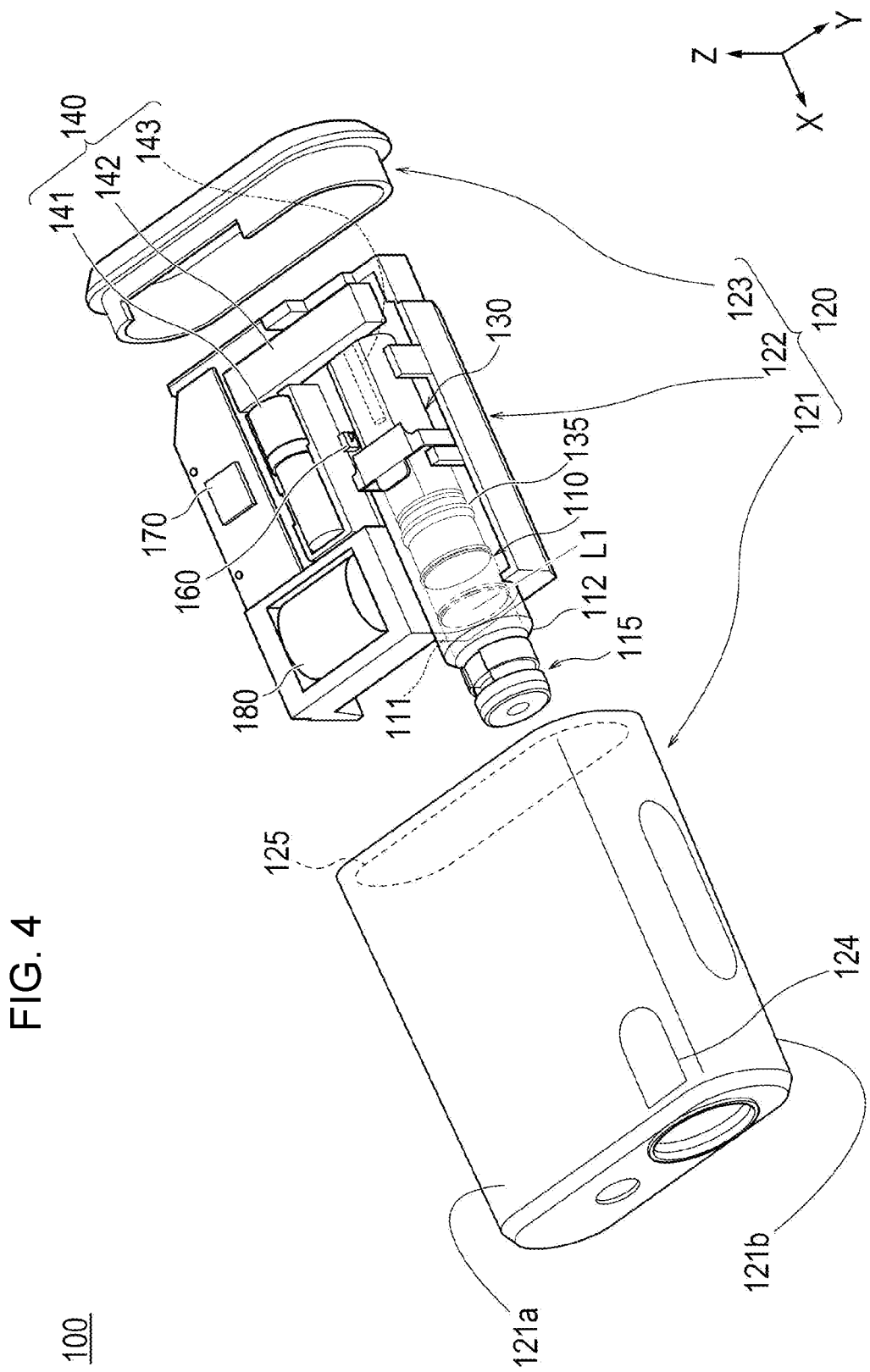
FIG. 4 is an exploded perspective view of the liquid medicine administration device illustrated in FIG. 1.
Figure 5:
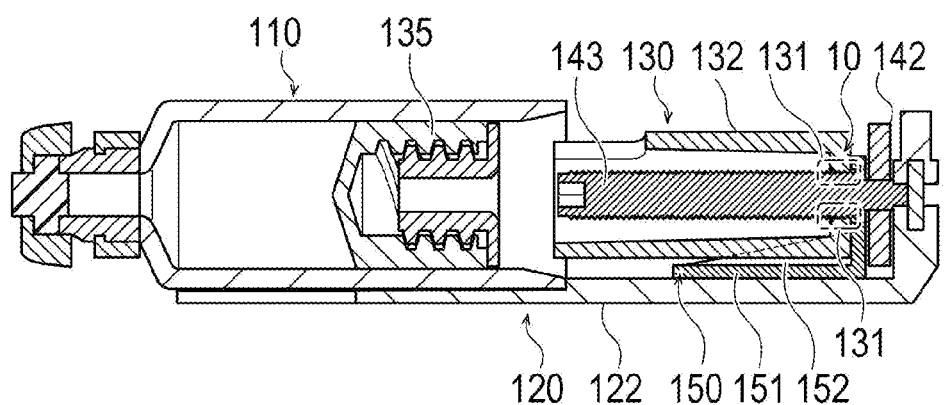
FIG. 5 is a sectional view illustrating a canceling mechanism of the liquid medicine administration device illustrated in FIG. 1 and a periphery thereof.

As illustrated in FIGS. 3 to 5, the liquid medicine administration device 100 includes: a liquid medicine container 110 filled with a liquid medicine; a plunger 130 that expels the liquid medicine in the liquid medicine container 110; a housing 120 that holds the liquid medicine container 110 and the plunger 130; a drive mechanism 140 that advances the plunger 130 toward a tip of the liquid medicine container 110; a rotation restriction unit 150 that restricts rotation of the plunger 130; a detector 160 that detects a position of the plunger 130; and a controller 170 that controls operations of the drive mechanism 140 and the detector 160.

As illustrated in FIGS. 3 and 4, the housing 120 has a box-shaped housing body 121 having a housing space formed therein, a chassis 122 that is housed in the housing space of the housing body 121 and can be fixed to the housing body 121, and a lid member 123 attached to the housing body 121 with the chassis 122 being housed in the housing space.

As illustrated in FIGS. 3 and 4, a window 124 is formed in an upper surface 121a of the housing body 121 to allow the inside of the housing space to be visible from the outside of the housing 120. The window 124 is formed by providing a transparent or semitransparent portion on a part of the housing body 121.

As illustrated in FIGS. 3 and 4, a base end opening 125 through which the chassis 122 is inserted into the housing space of the housing body 121 is formed in the base end of the housing body 121 in the longitudinal direction. The base end opening 125 of the housing body 121 is closed by the lid member 123 with the chassis 122 housed in the housing space.

A bottom surface 121b of the housing body 121 is provided with a sheet-shaped adhesive portion that can adhere to the body surface H of the user. In an initial state before the liquid medicine administration device 100 is attached to the user, a releasable protective sheet is attached to an adhesive surface of the adhesive portion.

As illustrated in FIG. 4, the chassis 122 holds the liquid medicine container 110, the plunger 130, the drive mechanism 140, the rotation restriction unit 150, the detector 160, the controller 170, and a power supply unit 180.

The liquid medicine container 110 is a so-called prefilled type liquid medicine container. Therefore, the liquid medicine is charged (located) in advance in a lumen 111 of the liquid medicine container 110. Examples of the liquid medicine include protein preparations, narcotic analgesics, and diuretics.

A sealing member for preventing the liquid medicine from leaking is disposed at a tip opening (discharge port) formed at a tip 112 of the liquid medicine container 110. As illustrated in FIG. 3, the tip 112 of the liquid medicine container 110 is disposed to protrude from the housing body 121 to the outside. In addition, a mounting portion 115 that is to be connected to a tube 240 (see FIG. 1) described later is attached to the tip of the liquid medicine container 110 that protrudes from the housing body 121.

As illustrated in FIG. 4, the plunger 130 is inserted into or positioned in the lumen 111 of the liquid medicine container 110. A gasket 135 slidable on an inner wall of the liquid medicine container 110 is disposed at a tip of the plunger 130. The outer periphery of the gasket 135 is in liquid-tight contact with the inner peripheral surface of the liquid medicine container 110, whereby the base end side of the gasket 135 is liquid-tightly sealed.

The plunger 130 is composed of a cylindrical member.

As illustrated in FIG. 5, the plunger 130 includes: a threaded portion 131 threadedly engaged with the feed screw 143; and a plunger body 132 that advances with the rotation of the feed screw 143 and presses (moves) the gasket 135, while rotation with respect to the housing 120 (chassis 122) is being restricted by the rotation restriction unit 150. The plunger body 132 has a notch (not illustrated) on a surface facing the chassis 122, and holds the rotation restriction unit 150 to be described later.

The plunger 130 is provided with a canceling mechanism 10 that cancels the transmission of the pressing force from the plunger body 132 to the gasket 135 when receiving an axial reaction force equal to or greater than a preset pressing force from the gasket 135 during advancement with the rotation of the feed screw 143. The structure of the canceling mechanism 10 will be described later. In the present specification, the preset pressing force means a force required to expel the liquid medicine in the liquid medicine container 110 by the plunger body 132 pressing the gasket 135 in a case where blockage does not occur in the liquid delivery path of the liquid medicine. In addition, the axial reaction force means a drag force in a direction opposite to the direction in which the plunger body 132 is advanced in the longitudinal direction (X direction) to expel the liquid medicine in the liquid medicine container 110.

As illustrated in FIG. 4, the drive mechanism 140 includes: a motor 141 that receives a drive current from the power supply unit 180 to generate a rotational driving force; a speed reduction mechanism 142 including a gear that transmits the rotational driving force of the motor 141, and the like; and a feed screw 143 connected to the speed reduction mechanism 142.

The feed screw 143 converts the rotary motion transmitted from the speed reduction mechanism 142 into a linear motion, and advances the plunger 130 in the longitudinal direction.

In the present embodiment, the plunger 130 advances in the longitudinal direction with the rotation of the feed screw 143, while the rotation of the plunger 130 with respect to the housing 120 is being restricted by the rotation restriction unit 150. As the plunger 130 advances toward the tip of the liquid medicine container 110, the liquid medicine in the lumen 111 of the liquid medicine container 110 is expelled to the tube 240 (see FIG. 1).

The rotation restriction unit 150 restricts rotation of the plunger 130 with respect to the housing 120. As illustrated in FIG. 5, the rotation restriction unit 150 has a bottom surface 151 fixed to the housing 120 and a guide wall 152 that restricts the rotation of the plunger 130 to urge the plunger 130 to advance in the longitudinal direction. The guide wall 152 is erected in the height direction (Z direction) from the bottom surface 151. The guide wall 152 is disposed so as to protrude into the internal space of the plunger 130 from a notch formed in a surface of the plunger 130 facing the chassis 122. In the present embodiment, the plunger 130 advances in the longitudinal direction with the rotation of the feed screw 143, while the rotation of the plunger 130 with respect to the housing 120 is being restricted by the rotation restriction unit 150. As the plunger 130 advances toward the tip of the liquid medicine container 110, the liquid medicine in the lumen 111 of the liquid medicine container 110 is expelled to the tube 240 (see FIG. 1).

As illustrated in FIG. 4, the detector 160 detects that the plunger 130 has advanced to a predetermined position L1. The predetermined position L1 can be set at any position in the longitudinal direction between a liquid delivery start position of the plunger 130 (the initial position of the plunger 130) to a liquid delivery end position (the position where the plunger 130 completely expels the liquid medicine in the liquid medicine container 110 to the tube 240).

The detector 160 can be constituted by, for example, a known contact sensor that transmits a predetermined electric signal when a detected portion provided at the base end of the plunger 130 comes into contact therewith.

The controller 170 controls the operation of delivering the liquid medicine by the liquid medicine administration device 100 on the basis of the detection result by the detector 160. The controller 170 can be implemented by, for example, a known microcomputer (electronic circuit element) mounted with a CPU, a RAM, a ROM, and the like. The controller 170 centrally controls operation of the drive mechanism 140, the detector 160, and the power supply unit 180.

In the present embodiment, the controller 170 determines that a predetermined amount of the liquid medicine is not expelled from the liquid medicine container 110 when a predetermined time has elapsed after a command to start the operation is given to the drive mechanism 140, and the detector 160 does not detect that the plunger 130 has advanced to the predetermined position L1. For example, the predetermined time can be set to be longer than a time during which the plunger 130 can sufficiently move to the predetermined position L1 after the controller 170 gives a command to start the operation to the drive mechanism 140 in a case where blockage does not occur in the liquid delivery path of the liquid medicine. When determining that a predetermined amount of the liquid medicine is not expelled, the controller 170 stops the motor 141 and notifies the user of the current situation.

The power supply unit 180 can be composed of, for example, a known battery.

Next, the structure of the canceling mechanism 10 will be described with reference to FIGS. 6A and 6B.

Figure 6A:
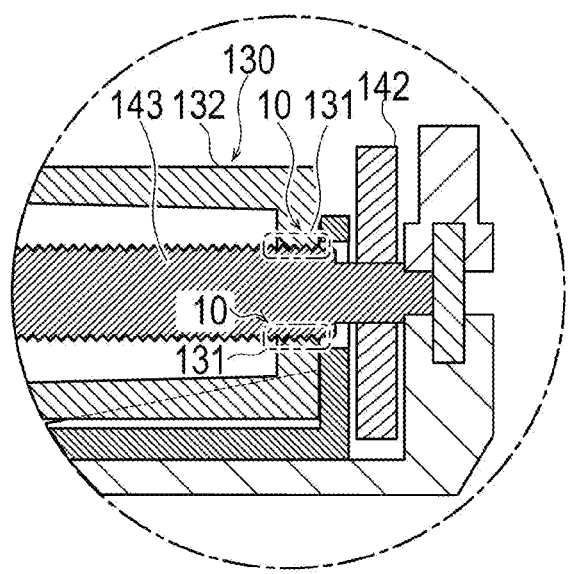
FIG. 6A is a partially enlarged view of the liquid medicine administration device illustrated in FIG. 5.
Figure 6B:
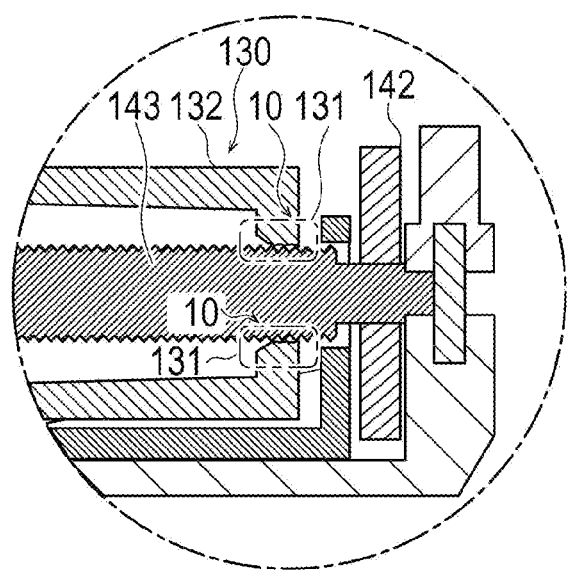
FIG. 6B is a partially enlarged view of the liquid medicine administration device illustrated in FIG. 5.

As illustrated in FIG. 6A, the canceling mechanism 10 includes a threaded portion 131. Therefore, the canceling mechanism 10 according to the present embodiment is threadedly engaged with the feed screw 143. When blockage occurs in the administration instrument 200 such as the tube 240 which is connectable to the liquid medicine administration device 100, the plunger 130 including the canceling mechanism 10 receives an axial reaction force equal to or greater than a preset pressing force from the gasket 135 (see FIG. 5). Therefore, a larger axial reaction force than that when no blockage occurs acts on the canceling mechanism 10 (threaded portion 131) from the feed screw 143. Accordingly, when blockage occurs, the canceling mechanism 10 (threaded portion 131) is worn by the feed screw 143 that rotates by the drive mechanism 140 to advance the plunger body 132 in the longitudinal direction as illustrated in FIG. 6B.

When the canceling mechanism 10 is worn by the feed screw 143, the feed screw 143 turns free with respect to the threaded portion 131. Therefore, the feed screw 143 cannot transmit the rotational driving force of the motor 141 to the plunger body 132. Accordingly, when blockage occurs in the liquid delivery path of the liquid medicine, the canceling mechanism 10 can cancel the transmission of the pressing force from the plunger 130 including the plunger body 132 to the gasket 135.

The material of the canceling mechanism 10 is not particularly limited, and a metal material or a resin material may be used as long as it is a soft material that is worn by the feed screw 143 when receiving an axial reaction force equal to or greater than a preset pressing force from the gasket 135.

The height of the screw thread of the canceling mechanism 10 may be lower or less than the height of the screw thread of the feed screw 143. With this configuration, the canceling mechanism 10 and the feed screw 143 are threadedly engaged with each other with their screw threads being lightly engaged with each other. Therefore, when the canceling mechanism 10 is worn by the feed screw 143, the screw thread of the feed screw 143 turns free earlier with respect to the threaded portion 131. Accordingly, the canceling mechanism 10 can further shorten the time from when the blockage occurs in the liquid delivery path of the liquid medicine until the transmission of the pressing force from the plunger body 132 to the gasket 135 is canceled.

(Administration Instrument)

As illustrated in FIGS. 1 and 2, the administration instrument 200 is connectable to the liquid medicine administration device 100.

The administration instrument 200 includes a connector 210, a needle tube 220 that is inserted into a living body, a puncture portion (cannula housing) 230, the tube 240, and a puncture assistance tool 250 that assists the puncture of the living body with the needle tube 220.

The connector 210 is connectable to the liquid medicine administration device 100 via a mounting portion 215 fixed to the connector 210. The mounting portion 215 can be connected to the liquid medicine administration device 100 by being externally fitted to the mounting portion 115 (see FIG. 4) which is provided at the tip 112 of the liquid medicine container 110 protruding to the outside of the housing 120.

The mounting portion 215 has inside a connecting needle capable of piercing a sealing member provided at the tip of the liquid medicine container 110.

The tube 240 communicates with the lumen 111 of the liquid medicine container 110 via the connecting needle.

A flow path that connects the tube 240 and the lumen of the needle tube 220 is formed inside the puncture portion 230. The liquid medicine delivered to the puncture portion 230 via the tube 240 is administered into the living body through the flow path formed inside the puncture portion 230 and the needle tube 220.

When the liquid medicine is delivered to the user, the puncture assistance tool 250 is attached to the puncture portion 230. The puncture assistance tool 250 holds an introducer needle (inner needle) 251. The introducer needle 251 projects from the tip of the needle tube 220 when the puncture assistance tool 250 is attached to the puncture portion 230. The user can insert the needle tube 220 into the living body, while preventing the needle tube 220 from having any troubles such as breakage, by piercing the living body with the needle tube 220 with the introducer needle 251 inserted into the needle tube 220.

The puncture assistance tool 250 is removed from the puncture portion 230 after the needle tube 220 is inserted into the living body. The introducer needle 251 is withdrawn from the lumen of the needle tube 220 when the puncture assistance tool 250 is removed from the puncture portion 230.

After the needle tube 220 is inserted into the living body, the puncture assistance tool 250 is removed, and the puncture portion 230 is left on the body surface H of the user with the needle tube 220 left in the living body. In this state, the plunger 130 of the liquid medicine administration device 100 advances in the liquid medicine container 110, so that the liquid medicine with which the liquid medicine container 110 is filled is delivered to the lumen of the needle tube 220 through the tube 240 and the flow path of the puncture portion 230.

The introducer needle 251 can be, for example, a metal needle. Further, the needle tube 220 can be composed of, for example, a tubular member (cannula) made of resin.

Similar to the liquid medicine administration device 100, the administration instrument 200 is of a patch type that is attached to the body surface H of the user when used. The contact surface (bottom surface) 231 of the puncture portion 230 of the administration instrument 200 is provided with a sheet-shaped adhesive portion that can adhere to the body surface. In an initial state before the administration instrument 200 is attached to the user, a releasable protective sheet is attached to an adhesive surface of the adhesive portion.

As described above, the liquid medicine administration device 100 according to the present embodiment includes: the liquid medicine container 110 filled with a liquid medicine and having, at a tip, an opening through which the liquid medicine can be discharged; the gasket 135 for expelling the liquid medicine in the liquid medicine container 110, the gasket 135 being slidable on the inner wall of the liquid medicine container 110; the plunger 130 capable of pressing the gasket 135; the housing 120 that holds the liquid medicine container 110 and the plunger 130; the drive mechanism 140 that advances the plunger 130 toward the tip of the liquid medicine container 110; and the rotation restriction unit 150 that restricts the rotation of the plunger 130 with respect to the housing 120. The drive mechanism 140 includes the motor 141 and the feed screw 143 that rotates in response to the rotation of the motor 141. The plunger 130 includes: the threaded portion 131 threadedly engaged with the feed screw 143; and the plunger body 132 that advances with the rotation of the feed screw 143 and presses the gasket 135, while the rotation of the plunger 130 with respect to the housing 120 is being restricted by the rotation restriction unit 150. The plunger 130 is provided with the canceling mechanism 10 that cancels the transmission of the pressing force from the plunger body 132 to the gasket 135 when the plunger body 132 receives an axial reaction force equal to or greater than a preset pressing force from the gasket 135 during advancement with the rotation of the feed screw 143.

According to the liquid medicine administration device 100, when blockage occurs in the liquid delivery path of the liquid medicine, the plunger 130 receives an axial reaction force equal to or greater than the preset pressing force from the gasket 135. The canceling mechanism 10 cancels the transmission of the pressing force from the plunger body 132 to the gasket 135 when the plunger 130 receives an axial reaction force equal to or greater than a preset pressing force from the gasket 135. As a result, the gasket 135 cannot obtain torque for advancement toward the tip of the liquid medicine container 110. Thus, the configuration described above can prevent leakage of the liquid medicine when blockage occurs in the liquid delivery path of the liquid medicine.

In addition, the canceling mechanism 10 includes the threaded portion 131. When receiving an axial reaction force from the gasket 135, the threaded portion 131 is worn by the feed screw 143, and the feed screw 143 turns free with respect to the threaded portion 131. Therefore, the feed screw 143 cannot transmit the rotational driving force of the motor 141 to the plunger body 132. Accordingly, when blockage occurs in the liquid delivery path of the liquid medicine, the canceling mechanism 10 can cancel the transmission of the pressing force from the plunger 130 including the plunger body 132 to the gasket 135. Thus, the configuration described above can prevent leakage of the liquid medicine when blockage occurs in the liquid delivery path of the liquid medicine.

The liquid medicine administration device 100 further includes the detector 160 detecting that the plunger 130 has advanced to the predetermined position L1, and the controller 170 that controls the start and stop of the operation of the drive mechanism 140. The controller 170 determines that a predetermined amount of the liquid medicine is not expelled from the liquid medicine container 110, when a predetermined time has elapsed after a command to start the operation is given to the drive mechanism 140, and the detector 160 does not detect that the plunger 130 has advanced to the predetermined position L1. Therefore, when blockage occurs in the liquid delivery path of the liquid medicine, the controller 170 can give a command to stop the operation of the drive mechanism 140 on the basis of the detection result by the detector 160. Thus, the configuration described above can prevent leakage of the liquid medicine when blockage occurs in the liquid delivery path of the liquid medicine.

While the liquid medicine administration device has been described above by way of the embodiment representing one example of the liquid medicine administration device, the present invention is not limited to each of the described configurations, and can be appropriately modified. A modification of the motor will now be described. In the description of the modification, a detailed description of the configuration and details of the liquid medicine administration system 1 described above will not be repeated.

<First Modification>

A liquid medicine administration device 100 according to the first modification uses a DC motor as a motor 141A for the purpose of miniaturization and cost reduction in order to facilitate handling at the time of use and to save a storage space at the time of storage. The DC motor is a coreless motor which is easily downsized and has high torque efficiency with respect to electric power. The DC motor has a characteristic that a current supplied to the DC motor and the rotation speed of the DC motor are different depending on the magnitude of a load torque. The controller 170 detects an administration abnormality (a situation in which a predetermined amount of the liquid medicine is not expelled from the liquid medicine container 110) using the characteristics of the motor 141A. Therefore, a controller 170A controls the drive mechanism 140 as follows.

Figure 7A:
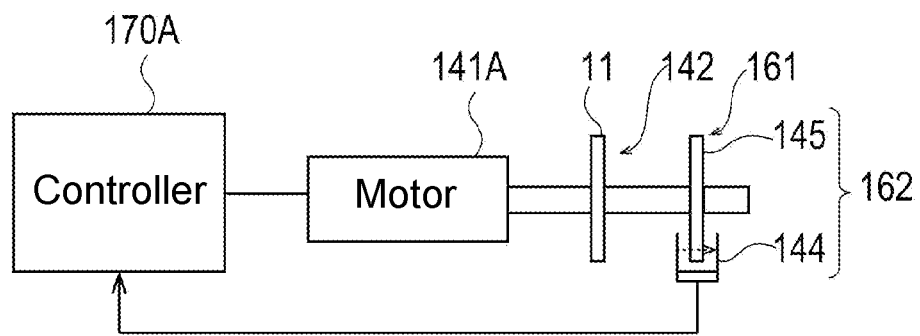
FIG. 7A is a block diagram of a control system of a liquid medicine administration device according to a first modification.
Figure 7B:
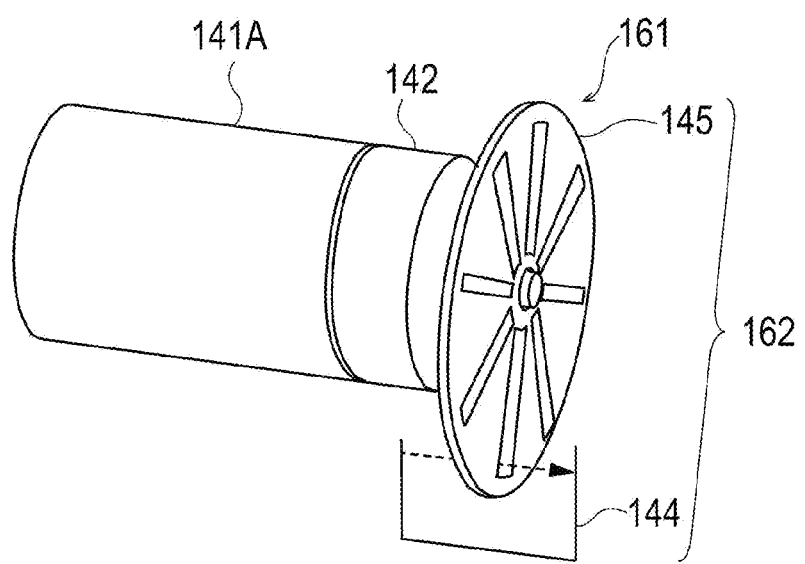
FIG. 7B is a diagram schematically illustrating a rotation detector and the like according to the first modification.
Figure 8:
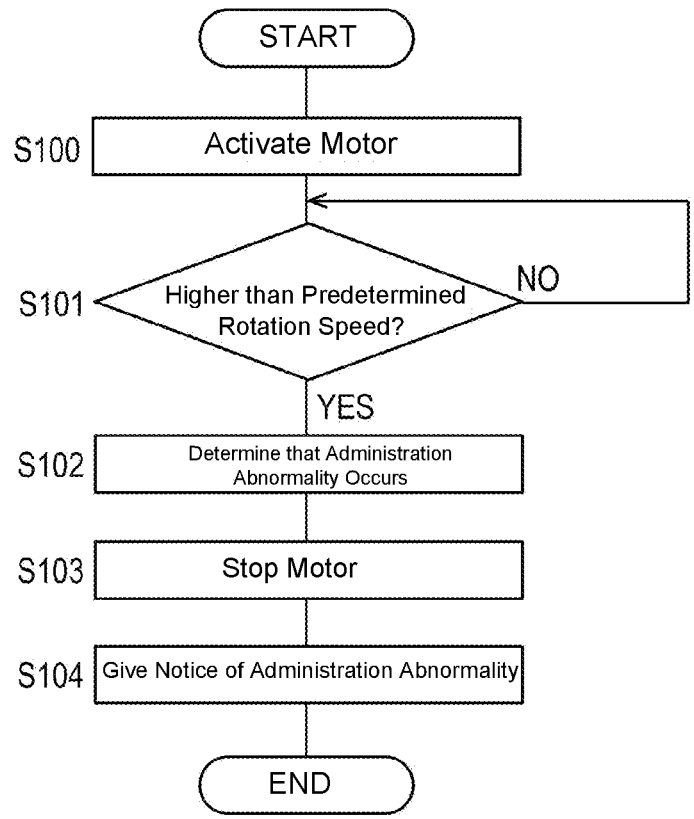
FIG. 8 is a flowchart illustrating operation of a controller according to the first modification.

A specific operation of the controller 170A will be described with reference to FIGS. 7A, 7B, and 8. FIG. 7A is a block diagram of a control system of the liquid medicine administration device 100 according to the first modification. FIG. 7B is a diagram schematically illustrating a rotation detector 161 and the like according to the first modification. FIG. 8 is a flowchart illustrating operation of the controller 170A according to the first modification.

As illustrated in FIG. 7A, the controller 170A is electrically connected to the motor 141A. A rotation shaft of the motor 141A is mechanically connected to the speed reduction mechanism 142. In the speed reduction mechanism 142, an encoder 162 is provided as a rotation detector 161 that detects the rotation speed of the motor 141A.

As illustrated in FIG. 7B, the encoder 162 includes a photointerrupter 144 including an optical sensor, and a slit plate 145 having a large number of slits which are radially formed. The rotation of the motor 141A is detected by detecting whether or not light passes through the slits of the slit plate 145 with the optical sensor of the photointerrupter 144. The photointerrupter 144 is electrically connected to the controller 170A. In the present embodiment, the encoder 162 using the photointerrupter 144 is described as an example of the rotation detector 161, but an encoder using a magnetic sensor may be used.

When the controller 170A rotates the motor 141A, the speed reduction mechanism 142 is driven, so that the plunger 130 advances in the liquid medicine container 110 (see FIG. 4). At this time, the encoder 162 provided adjacent to the speed reduction mechanism 142 detects the rotation of the motor 141A, and the controller 170A calculates the rotation speed of the motor 141A on the basis of the rotation of the motor 141A detected by the encoder 162. The rotation of the motor 141A detected by the encoder 162 is fed back to the controller 170A, and the controller 170A calculates the rotation speed of the motor 141A or determines whether or not the motor 141A is rotating on the basis of the feedback result. The rotation detector 161 can also be provided as a part of the speed reduction mechanism 142 Specifically, the slit plate 145 is eliminated, and instead, a large number of slits are radially provided in the gear of the speed reduction mechanism 142. The optical sensor of the photointerrupter 144 detects whether or not light passes through the slits provided in the gear, whereby the rotation of the motor 141A is detected. In this case, the encoder 162 is constituted by the gear of the speed reduction mechanism 142 and the photointerrupter 144. With this configuration, the liquid medicine with which the liquid medicine container 110 is filled is delivered to the lumen of the needle tube 220 via the liquid delivery path of the liquid medicine such as the tube 240 and the puncture portion 230, and is administered to the living body.

As illustrated in FIG. 8, the controller 170A activates the motor 141A at the time of administering the liquid medicine to the living body (S100), and determines whether or not the rotation speed of the motor 141A is higher than a predetermined rotation speed (S101). The rotation speed of the motor 141A at the time of administering the liquid medicine to the living body is set in advance according to the rate of administration of the liquid medicine. When the rotation speed of the motor 141A is lower than (not higher than) the predetermined rotation speed (S101: NO), it can be determined that the liquid medicine is normally administered, so that the administration of the liquid medicine is continued. On the other hand, when the rotation speed of the motor 141A is higher than the predetermined rotation speed (exceeds the predetermined rotation speed), it is considered that the plunger body 132 receives an axial reaction force equal to or greater than the pressing force from the gasket 135 due to an occurrence of an abnormality such as blockage of the liquid delivery path of the liquid medicine, resulting in that the transmission of the pressing force from the plunger 130 including the plunger body 132 to the gasket 135 is canceled by the canceling mechanism 10, and the load on the motor 141A is reduced (S101: YES). Therefore, the controller 170A detects an administration abnormality (S102). Next, the controller 170A stops the motor 141A (S103) and notifies the user of the administration abnormality (S104). The administration abnormality may be notified by lighting or blinking an LED provided on a case of the liquid medicine administration device 100, or by outputting a sound from a speaker provided inside the case of the liquid medicine administration device 100. In addition, the occurrence of the administration abnormality may be wirelessly reported to an external computer.

As described above, in the liquid medicine administration device 100 according to the first modification, the motor 141A is a DC motor. The liquid medicine administration device 100 further includes the rotation detector 161 that detects rotation of the DC motor and the controller 170A that controls rotation of the DC motor. The controller 170A stops the rotation of the motor 141A when the rotation speed of the motor 141A calculated based on the rotation of the motor 141A detected by the rotation detector 161 becomes equal to or higher than a predetermined speed. Therefore, in a case where blockage occurs in the liquid delivery path of the liquid medicine, the controller 170A can prevent the motor 141A from being continuously driven on the basis of the detection result of the detector 160. Thus, the configuration described above can prevent leakage of the liquid medicine when blockage occurs in the liquid delivery path of the liquid medicine.

While an example of the configuration of a medical device has been described above, the present invention is not limited to the description of the above embodiment, and various modifications are possible without departing from the invention.

<Second Modification>

Figure 9A:
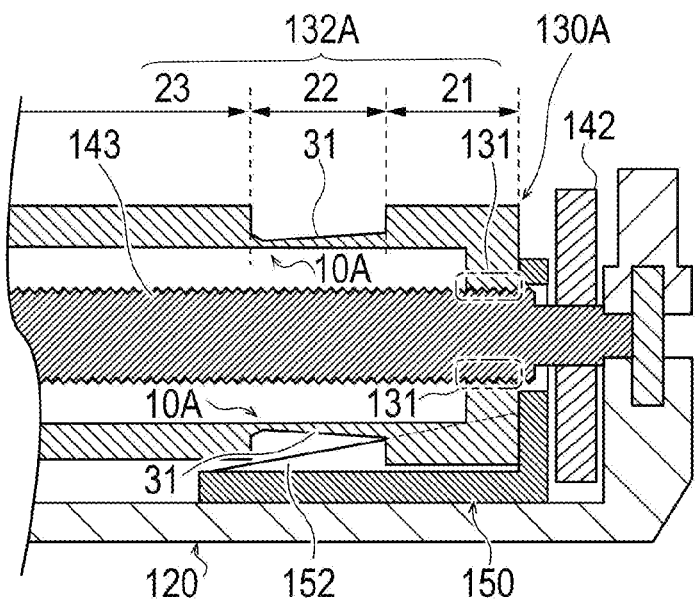
FIG. 9A is a partially enlarged sectional view illustrating a canceling mechanism and its periphery according to a second modification.
Figure 9B:
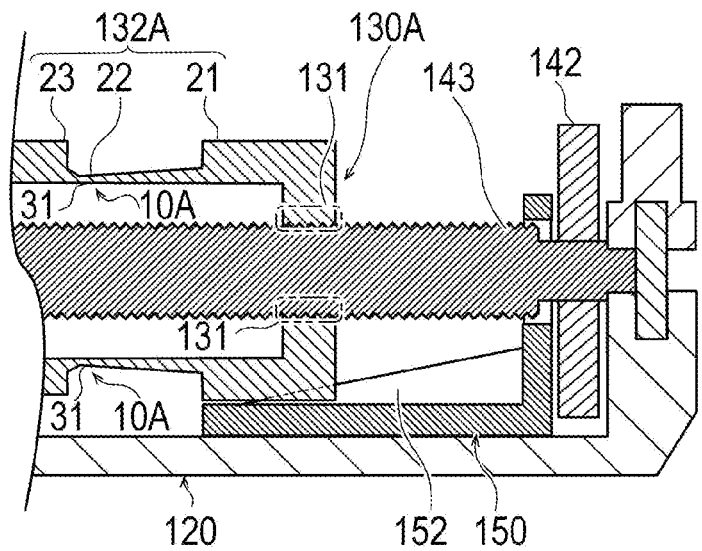
FIG. 9B is a partially enlarged sectional view illustrating the canceling mechanism and its periphery according to the second modification.
Figure 9C:
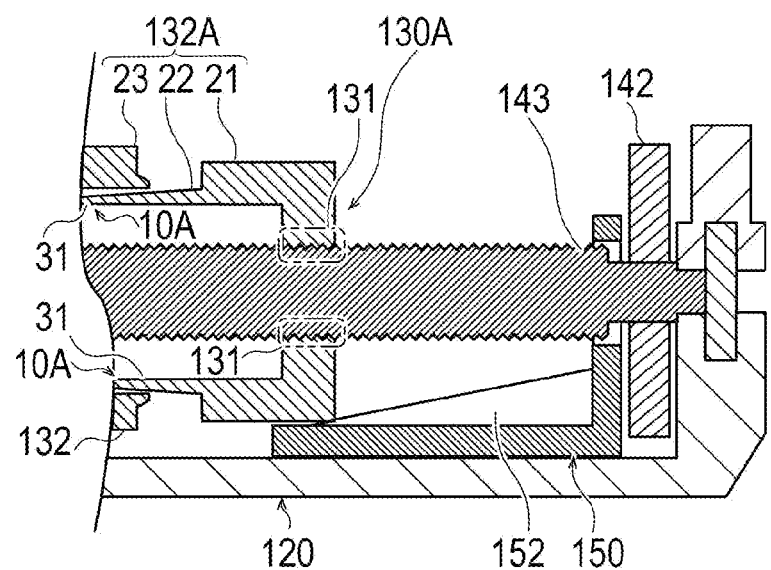
FIG. 9C is a partially enlarged sectional view illustrating the canceling mechanism and its periphery according to the second modification.

Next, modifications of the plunger and the canceling mechanism will be described by way of a second modification and a third modification. A liquid medicine administration device 100 according to the second modification includes a plunger 130A and a canceling mechanism 10A having structures different from those of the plunger 130 and the canceling mechanism 10 according to the above embodiment. FIGS. 9A to 9C are diagrams for describing the plunger 130A and the canceling mechanism 10A according to the second modification.

The plunger 130A includes a plunger body 132A.

As illustrated in FIGS. 9A to 9C, the plunger body 132A includes a base end portion 21 having a threaded portion 131, a tip portion 23 that is in contact with the gasket 135 (see FIG. 5), and an intermediate portion 22 formed between the base end portion 21 and the tip portion 23.

The canceling mechanism 10A has a thin portion (thinned portion) 31 formed in the intermediate portion 22 of the plunger body 132A.

As illustrated in FIGS. 9A and 9B, the plunger body 132A advances with the rotation of the feed screw 143 connected to the speed reduction mechanism 142, while rotation with respect to the housing 120 is being restricted by the rotation restriction unit 150.

When blockage occurs in the liquid delivery path of the liquid medicine, the thin portion 31 is bent or broken in a direction intersecting the direction in which the plunger body 132A advances. FIG. 9C illustrates an example in which the thin portion 31 is broken in a direction intersecting the direction in which the plunger body 132A advances.

The state in which the thin portion 31 is bent means that, for example, when the plunger body 132A receives an axial reaction force equal to or greater than a preset pressing force from the gasket 135 (see FIG. 5), the plunger body 132A is bent (breaks) at the thin portion 31 in a direction intersecting the axial direction, and the plunger body 132A is compressed and deformed in the axial direction, resulting in that the distance between the base end portion 21 and the tip portion 23 is decreased. In this case, the advancement of the tip portion 23 is stopped with respect to the base end portion 21 that continues to advance. Then, when the base end portion 21 of the plunger 130A continues to advance, the base end portion 21 is disengaged from the guide wall 152 of the rotation restriction unit 150 and turns free with respect to the housing 120. Therefore, the plunger 130A rotates together with the feed screw 143 without advancing. Accordingly, the canceling mechanism 10A (thin portion 31) can prevent the transmission of the pressing force from the plunger body 132A to the gasket 135.

The minimum thickness of the thin portion 31 is not particularly limited as long as it allows the thin portion 31 to be easily bent (broken) when blockage occurs in the liquid delivery path of the liquid medicine.

As described above, the plunger body 132A of the liquid medicine administration device 100 according to the second modification includes the base end portion 21 having the threaded portion 131, the tip portion 23 that is in contact with the gasket 135, and the intermediate portion 22 formed between the base end portion 21 and the tip portion 23. The canceling mechanism 10A has a thin portion 31 formed in the intermediate portion 22 of the plunger body 132A. When receiving the axial reaction force from the gasket 135, the thin portion 31 is bent or broken in a direction intersecting the direction in which the plunger body 132A advances. Therefore, the distance between the base end portion 21 and the tip portion 23 of the plunger body 132A is decreased due to the thin portion 31 being bent or broken, and the restriction of rotation of the plunger 130A with respect to the housing 120 by the rotation restriction unit 150 is removed. Thus, the advancement of the plunger body 132A with the rotation of the feed screw 143 is stopped.

According to the liquid medicine administration device 100 described above, when the plunger body 132A receives an axial reaction force from the gasket 135, the plunger body 132A is bent at the thin portion 31 in a direction intersecting the axial direction, and the advancement of the tip portion 23 is stopped with respect to the base end portion 21 that continues to advance. Then, the base end portion 21 is freed from the restriction of rotation by the rotation restriction unit 150. Therefore, the plunger 130A rotates together with the feed screw 143 without advancing. Accordingly, the canceling mechanism 10A including the thin portion 31 can prevent the transmission of the pressing force from the plunger body 132A to the gasket 135. Thus, the configuration described above can prevent leakage of the liquid medicine when blockage occurs in the liquid delivery path of the liquid medicine.

<Third Modification>

Figure 10A:
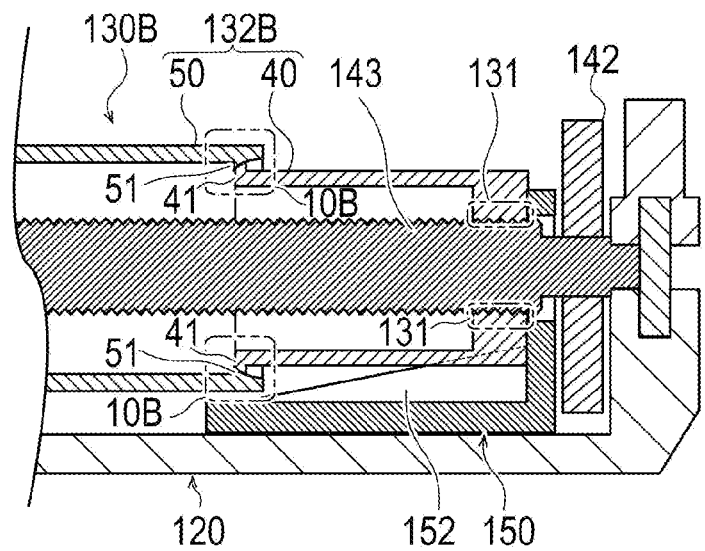
FIG. 10A is a partially enlarged sectional view illustrating a canceling mechanism and its periphery according to a third modification.
Figure 10B:
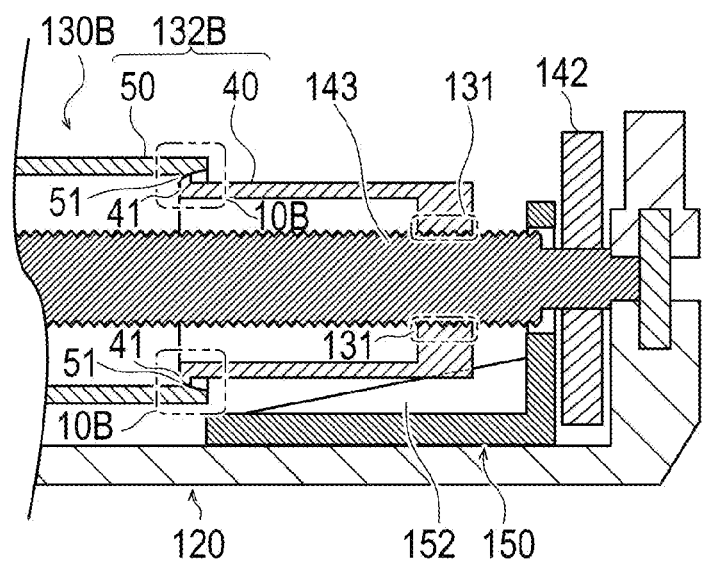
FIG. 10B is a partially enlarged sectional view illustrating the canceling mechanism and its periphery according to the third modification.
Figure 10C:
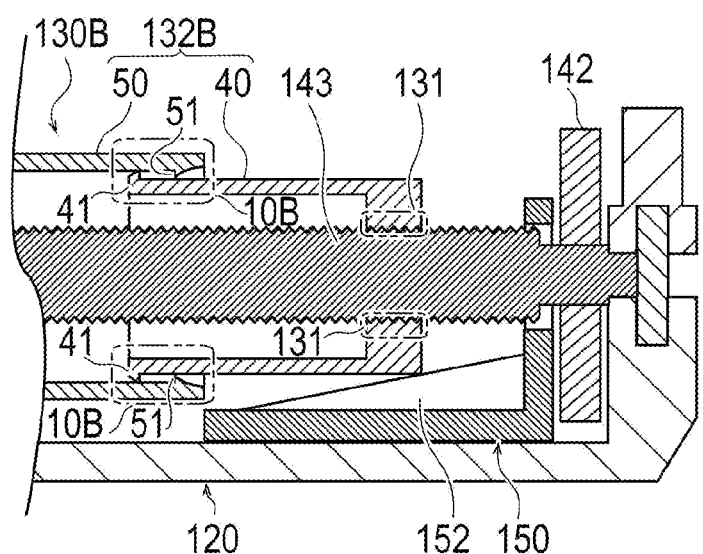
FIG. 10C is a partially enlarged sectional view illustrating the canceling mechanism and its periphery according to the third modification.

Next, a liquid medicine administration device 100 according to the third modification will be described with reference to FIGS. 10A to 10C. The liquid medicine administration device 100 according to the third modification includes a plunger 130B and a canceling mechanism 10B having structures different from those of the plunger 130 and the canceling mechanism 10 according to the above embodiment. FIGS. 10A to 10C illustrate the plunger 130B and the canceling mechanism 10B according to the third modification.

The plunger 130B includes a plunger body 132B. As illustrated in FIGS. 10A to 10C, the plunger body 132B includes: an intermediate member 40 including the threaded portion 131 and a first protrusion 41; and a pressing member 50 including a second protrusion 51 and capable of pressing the gasket 135 (see FIG. 5).

The canceling mechanism 10B has the first protrusion 41 and the second protrusion 51.

As illustrated in FIGS. 10A and 10B, when the first protrusion 41 of the intermediate member 40 and the second protrusion 51 of the pressing member 50 contact each other, the plunger body 132B advances with the rotation of the feed screw 143 connected to the speed reduction mechanism 142, while rotation with respect to the housing 120 is being restricted by the rotation restriction unit 150.

On the other hand, when blockage occurs in the liquid delivery path of the liquid medicine, the first protrusion 41 of the intermediate member 40 climbs over the second protrusion 51 of the pressing member 50 in the direction in which the pressing member 50 advances as illustrated in FIG. 10C.

The state in which the first protrusion 41 climbs over the second protrusion 51 means that, for example, when the plunger body 132B receives an axial reaction force equal to or greater than a preset pressing force from the gasket 135 (see FIG. 5), the vicinity of the first protrusion 41 in the intermediate member 40 is bent in a radially inward direction intersecting the axial direction by the axial reaction force. In this case, the advancement of the pressing member 50 is stopped with respect to the intermediate member 40 that continues to advance. Then, when the intermediate member 40 of the plunger 130B continues to advance, the intermediate member 40 is disengaged from the guide wall 152 of the rotation restriction unit 150 and turns free with respect to the housing 120. Therefore, the plunger 130B rotates together with the feed screw 143 without advancing. Accordingly, the canceling mechanism 10B can prevent the transmission of the pressing force from the plunger body 132B to the gasket 135.

As described above, the plunger body 132B of the liquid medicine administration device 100 according to the third modification includes: the intermediate member 40 including the threaded portion 131 and the first protrusion 41; and the pressing member 50 including the second protrusion 51 contactable to the first protrusion 41 of the intermediate member 40 and capable of pressing the gasket 135. The canceling mechanism 10B has the first protrusion 41 of the intermediate member 40 and the second protrusion 51 of the pressing member 50. The plunger body 132B advances with the rotation of the feed screw 143 due to the contact between the first protrusion 41 of the intermediate member 40 and the second protrusion 51 of the pressing member 50, while rotation with respect to the housing 120 is being restricted by the rotation restriction unit 150. When the plunger body 132B receives the axial reaction force from the gasket 135, the first protrusion 41 of the intermediate member 40 climbs over the second protrusion 51 of the pressing member 50 in the direction in which the pressing member 50 advances, so that the contact between the first protrusion 41 of the intermediate member 40 and the second protrusion 51 of the pressing member 50 is released, and the advancement of the plunger body 132B with the rotation of the feed screw 143 is stopped.

According to the liquid medicine administration device 100, when the plunger body 132B receives the axial reaction force from the gasket 135, the vicinity of the first protrusion 41 in the intermediate member 40 is bent in a radially inward direction intersecting the axial direction by the axial reaction force, and the advancement of the pressing member 50 is stopped with respect to the intermediate member 40 that continues to advance. Then, the intermediate member 40 is freed from the restriction of rotation by the rotation restriction unit 150. Therefore, the plunger 130B rotates together with the feed screw 143 without advancing. Accordingly, the canceling mechanism 10B can prevent the transmission of the pressing force from the plunger body 132B to the gasket 135. Thus, the configuration described above can prevent leakage of the liquid medicine when blockage occurs in the liquid delivery path of the liquid medicine.

The detailed description above describes embodiments of a liquid medicine administration device representing examples of the inventive liquid medicine administration device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A liquid medicine administration device comprising:
    a liquid medicine container filled with a liquid medicine, the liquid medicine container including a tip at which is located an opening through which the liquid medicine is to be discharged during administration of the liquid medicine;
    a gasket for expelling the liquid medicine in the liquid medicine container along a liquid delivery path, the gasket being slidable on an inner wall of the liquid medicine container to move in the liquid medicine container and discharge the liquid medicine through the opening;
    a plunger connected to the gasket;
    a housing that holds the liquid medicine container and the plunger;
    a drive mechanism that advances the plunger toward the tip of the liquid medicine container;
    a rotation restriction unit that restricts rotation of the plunger with respect to the housing;
    the drive mechanism including a motor that produces a drive torque, and a feed screw that rotates in response to the drive torque;
    the plunger including a threaded portion threadedly engaged with the feed screw, and a plunger body that advances in the liquid medicine container toward the tip by virtue of the rotation of the feed screw that is threadedly engaged with the threaded portion of the plunger and the rotation restriction unit that restricts rotation of the plunger with respect to the housing;

the plunger body including a base end portion having the threaded portion, a tip portion that is in contact with the gasket, and an intermediate portion between the base end portion and the tip portion;

the plunger including a canceling mechanism that cancels transmission of a pressing force from the plunger body to the gasket when the plunger body receives an axial reaction force equal to or greater than a preset pressing force from the gasket when a blockage occurs in the liquid delivery path of the liquid medicine during advancement of the gasket by the rotation of the feed screw;

the canceling mechanism including a thinned portion in the intermediate portion of the plunger body, the thinned portion being configured to be bent or broken in a direction intersecting a direction in which the plunger body advances when receiving the axial reaction force equal to or greater than the preset pressing force from the gasket so that the plunger body rotates together with the feed screw without advancing; and the bending or breaking of the thinned portion causing a decrease in a distance between the base end portion and the tip portion of the plunger body, removal of the restriction of rotation of the plunger with respect to the housing by the rotation restriction unit, and stopping of the advancement of the plunger body with the rotation of the feed screw.

2. The liquid medicine administration device according to claim 1, further comprising:
   a detector configured to detect that the plunger has advanced to a predetermined position; and
   a controller configured to control start and end of operation of the drive mechanism,
   the controller being configured to determine that a predetermined amount of the liquid medicine has not been expelled from the liquid medicine container, when a predetermined time has elapsed after a command to start the operation is given to the drive mechanism and when the detector does not detect that the plunger has advanced to the predetermined position.

3. The liquid medicine administration device according to a claim 1, wherein
   the motor is a DC motor,
   the liquid medicine administration device further includes a rotation detector that detects rotation of the DC motor, and a controller that controls the rotation of the DC motor, and
   the controller is configured to stop rotation of the DC motor when a rotation speed of the DC motor calculated based on the rotation of the DC motor detected by the rotation detector becomes equal to or higher than a predetermined speed.

4. The liquid medicine administration device according to claim 3, further comprising:
   a detector configured to detect that the plunger has advanced to a predetermined position; and
   a controller configured to control start and end of operation of the drive mechanism,
   the controller being configured to determine that a predetermined amount of the liquid medicine has not been expelled from the liquid medicine container, when a predetermined time has elapsed after a command to start the operation is given to the drive mechanism and when the detector does not detect that the plunger has advanced to the predetermined position.

5. A liquid medicine administration device comprising:
   a liquid medicine container filled with liquid medicine, the liquid medicine container including a tip at which is located an opening through which the liquid medicine is discharged during administration of the liquid medicine;
   a gasket positioned inside the liquid medicine container and connected to a plunger, the gasket being movable in the liquid medicine container toward the opening of the liquid medicine container to discharge the liquid medicine through the opening and along a liquid delivery path;
   a housing in which is housed the liquid medicine container and the plunger;
   a motor which operates to output a drive torque, the motor being operatively connected to a feed screw so that the drive torque rotates the feed screw;
   at least one guide wall that engages the plunger to restrict rotation of the plunger relative to the housing;
   the plunger including a threaded portion and a plunger body, the threaded portion of the plunger threadedly engaging the feed screw, the plunger body being movable in the liquid medicine container toward the tip by virtue of the rotation of the feed screw that is threadedly engaged with the threaded portion of the plunger and the at least one guide wall that engages the plunger to restrict rotation of the plunger with respect to the housing;
   the plunger body receiving an axial reaction force equal to or greater than a preset pressing force from the gasket when a blockage occurs in the liquid delivery path of the liquid medicine while the plunger body is being advanced by the rotation of the feed screw; and
   the threaded portion of the plunger and the feed screw being configured so that when the blockage occurs in the liquid delivery path while the plunger body is being advanced by the rotation of the feed screw, the axial reaction force that is received by the plunger body and that is equal to or greater than the preset pressing force causes the threaded portion to become worn by the feed screw such that the feed screw turns freely relative to the threaded portion of the plunger and advancement of the gasket toward the tip ceases.

6. The liquid medicine administration device according to claim 5, further comprising:
   a detector configured to detect that the plunger has advanced to a predetermined position;
   a controller configured to control start and end of operation of the drive mechanism; and
   the controller being configured to determine that a predetermined amount of the liquid medicine has not been expelled from the liquid medicine container, when a predetermined time has elapsed after a command to start the operation is given to the drive mechanism and when the detector does not detect that the plunger has advanced to the predetermined position.

7. The liquid medicine administration device according to a claim 5, wherein the motor is a DC motor, and the liquid medicine administration device further includes a rotation detector that detects rotation of the DC motor and a controller that controls the rotation of the DC motor, the controller being configured to stop rotation of the DC motor when a rotation speed of the DC motor calculated based on the rotation of the DC motor detected by the rotation detector becomes equal to or higher than a predetermined speed.

8. A method comprising:

inserting a needle tube into a living body, the needle tube being connected to a liquid medicine container containing liquid medicine so that sliding movement of a gasket connected to a plunger and positioned in the liquid medicine container causes the liquid medicine to flow along a liquid delivery path from the liquid medicine container to the needle tube, the liquid medicine container being housed in a housing together with a motor that outputs a drive torque and that is operatively connected to a feed screw so that the drive torque rotates the feed screw, rotation of the plunger being restricted, the plunger including a threaded portion and a plunger body, the threaded portion of the plunger threadedly engaging the feed screw, the plunger body being movable in the liquid medicine container toward the tip by virtue of the rotation of the feed screw and the restriction on rotation of the plunger, operating the motor to produce the drive torque, and transferring the drive torque to the feed screw to move the plunger so that the plunger body applies a pressing force to the gasket to discharge liquid medicine from the liquid medicine container and along the liquid delivery path by way of the tip; and cancelling the pressing force applied by the plunger body to the gasket when a blockage occurs in the liquid delivery path and when the blockage in the liquid delivery path causes the plunger body to receive an axial reaction force equal to or greater than a preset pressing force from the gasket, and the cancellation of the pressing force applied by the plunger body to the gasket causing the gasket to stop moving toward the tip and causing the discharge of the liquid medicine from the liquid medicine container by way of the tip to stop.

9. The method according to claim 8, further comprising:

detecting that the plunger has advanced to a predetermined position; and determining that a predetermined amount of the liquid medicine has not been expelled from the liquid medicine container, when a predetermined time has elapsed after a command to start operation is given to the motor and when the detector does not detect that the plunger has advanced to the predetermined position.

10. A liquid medicine administration device comprising:

a liquid medicine container filled with a liquid medicine, the liquid medicine container including a tip at which is located an opening through which the liquid medicine is to be discharged during administration of the liquid medicine;

a gasket for expelling the liquid medicine in the liquid medicine container along a liquid delivery path, the gasket being slidable on an inner wall of the liquid medicine container to move in the liquid medicine container and discharge the liquid medicine through the opening;

a plunger connected to the gasket;

a housing that holds the liquid medicine container and the plunger;

a drive mechanism that advances the plunger toward the tip of the liquid medicine container;

a rotation restriction unit that restricts rotation of the plunger with respect to the housing;

the drive mechanism including a motor that produces a drive torque, and a feed screw that rotates in response to the drive torque;

the plunger including a threaded portion threadedly engaged with the feed screw, and a plunger body that advances in the liquid medicine container toward the tip by virtue of the rotation of the feed screw that is threadedly engaged with the threaded portion of the plunger and the rotation restriction unit that restricts rotation of the plunger with respect to the housing;

the plunger body including an intermediate member having the threaded portion and a first protrusion;

the plunger body including a pressing member that includes a second protrusion contactable to the first protrusion of the intermediate member and that is configured to press the gasket;

the plunger including a canceling mechanism that cancels transmission of a pressing force from the plunger body to the gasket when the plunger body receives an axial reaction force equal to or greater than a preset pressing force from the gasket when blockage occurs in the liquid delivery path of the liquid medicine during advancement of the gasket by the rotation of the feed screw;

the canceling mechanism including the first protrusion of the intermediate member and the second protrusion of the pressing member;

the plunger body being configured to advance with the rotation of the feed screw due to contact between the first protrusion of the intermediate member and the second protrusion of the pressing member, while the rotation of the plunger with respect to the housing is restricted by the rotation restriction unit; and when the plunger body receives the axial reaction force from the gasket that is equal to or greater than the preset pressing force, the first protrusion of the intermediate member climbs over the second protrusion of the pressing member in a direction in which the pressing member advances, so that the contact between the first protrusion of the intermediate member and the second protrusion of the pressing member is released, and the plunger body continues rotating together with the feed screw without advancing so that the advancement of the plunger body by the rotation of the feed screw is stopped.

11. The liquid medicine administration device according to claim 10, further comprising:

a detector configured to detect that the plunger has advanced to a predetermined position; and a controller configured to control start and end of operation of the drive mechanism, the controller being configured to determine that a predetermined amount of the liquid medicine has not been expelled from the liquid medicine container, when a predetermined time has elapsed after a command to start the operation is given to the drive mechanism and when the detector does not detect that the plunger has advanced to the predetermined position.

12. The liquid medicine administration device according to a claim 10, wherein the motor is a DC motor, the liquid medicine administration device further includes a rotation detector that detects rotation of the DC motor, and a controller that controls the rotation of the DC motor, and the controller is configured to stop rotation of the DC motor when a rotation speed of the DC motor calculated based on the rotation of the DC motor detected by the rotation detector becomes equal to or higher than a predetermined speed.

13. The liquid medicine administration device according to a claim 11, wherein
the motor is a DC motor,
the liquid medicine administration device further includes a rotation detector that detects rotation of the DC motor, and a controller that controls the rotation of the DC motor, and
the controller is configured to stop rotation of the DC motor when a rotation speed of the DC motor calculated based on the rotation of the DC motor detected by the rotation detector becomes equal to or higher than a predetermined speed.

14. The liquid medicine administration device according to claim 10, further comprising:
a detector configured to detect that the plunger has advanced to a predetermined position; and
a controller configured to control start and end of operation of the drive mechanism,
the controller being configured to determine that a predetermined amount of the liquid medicine has not been expelled from the liquid medicine container, when a predetermined time has elapsed after a command to start the operation is given to the drive mechanism and when the detector does not detect that the plunger has advanced to the predetermined position.

15. The liquid medicine administration device according to a claim 14, wherein
the motor is a DC motor,
the liquid medicine administration device further includes a rotation detector that detects rotation of the DC motor, and a controller that controls the rotation of the DC motor, and
the controller is configured to stop rotation of the DC motor when a rotation speed of the DC motor calculated based on the rotation of the DC motor detected by the rotation detector becomes equal to or higher than a predetermined speed.

16. The liquid medicine administration device according to a claim 1, further comprising a mounting portion connectable to a mounting part of an administration instrument that includes a tube fluidly connected to a needle tube that is configured to be inserted into a living body, the mounting portion being located at the tip of the liquid medicine container.

17. The liquid medicine administration device according to a claim 16, wherein the tip of the liquid medicine container extends through an opening in the housing and the mounting portion is positioned exteriorly of the housing.

18. The liquid medicine administration device according to a claim 5, further comprising a mounting portion connectable to a mounting part of an administration instrument that includes a tube fluidly connected to a needle tube that is configured to be inserted into a living body, the mounting portion being located at the tip of the liquid medicine container.

19. The liquid medicine administration device according to a claim 18, wherein the tip of the liquid medicine container extends through an opening in the housing and the mounting portion is positioned exteriorly of the housing.

20. The liquid medicine administration device according to a claim 10, further comprising a mounting portion connectable to a mounting part of an administration instrument that includes a tube fluidly connected to a needle tube that is configured to be inserted into a living body, the mounting portion being located at the tip of the liquid medicine container, the tip of the liquid medicine container extending through an opening in the housing and the mounting portion being positioned exteriorly of the housing.

* * * * *